(12) United States Patent
Xu

(10) Patent No.: US 7,591,806 B2
(45) Date of Patent: Sep. 22, 2009

(54) HIGH-ASPECT-RATIO MICRODEVICES AND METHODS FOR TRANSDERMAL DELIVERY AND SAMPLING OF ACTIVE SUBSTANCES

(76) Inventor: Bai Xu, 116 Kennewyck Cir., Slingerlands, NY (US) 12159

( * ) Notice: Subject to any disclaimer, the term of this patent is extended or adjusted under 35 U.S.C. 154(b) by 102 days.

(21) Appl. No.: 10/908,584

(22) Filed: May 18, 2005

(65) Prior Publication Data

US 2005/0261632 A1 Nov. 24, 2005

Related U.S. Application Data

(60) Provisional application No. 60/521,540, filed on May 18, 2004.

(51) Int. Cl.
    *B29C 33/40* (2006.01)
(52) U.S. Cl. ............... 604/272; 604/890.1; 438/689
(58) Field of Classification Search ........... 604/171, 604/272, 219; 424/451; 606/185; 216/41; 438/706
See application file for complete search history.

(56) References Cited

U.S. PATENT DOCUMENTS

| | | | |
|---|---|---|---|
| 3,221,740 A | 12/1965 | Rosenthal | |
| 3,675,766 A | 7/1972 | Rosenthal | |
| 3,964,482 A | 6/1976 | Gerstel et al. | |
| 4,159,659 A | 7/1979 | Nightingale | |
| 4,222,392 A | 9/1980 | Brennan | |
| 4,286,599 A | 9/1981 | Hahn et al. | |
| 4,340,048 A | 7/1982 | Eckenhoff | |
| 4,381,963 A | 5/1983 | Goldstein et al. | |
| 4,592,753 A | 6/1986 | Panoz | |
| 4,921,475 A | 5/1990 | Sibalis | |
| 4,938,759 A | 7/1990 | Enscore et al. | |
| 5,139,029 A | 8/1992 | Fishman et al. | |
| 5,156,591 A | 10/1992 | Gross et al. | |
| 5,401,242 A | 3/1995 | Yacowitz | |
| 5,527,288 A | 6/1996 | Gross et al. | |
| 5,591,139 A | 1/1997 | Lin et al. | |
| 5,801,057 A | 9/1998 | Smart et al. | |
| 5,843,114 A | 12/1998 | Jang | |
| 5,855,801 A | 1/1999 | Lin et al. | |
| 5,879,326 A | 3/1999 | Godshall et al. | |
| 5,928,207 A | 7/1999 | Pisano et al. | |
| 6,050,988 A | 4/2000 | Zuck | |
| 6,451,240 B1 * | 9/2002 | Sherman et al. | 264/504 |
| 6,503,231 B1 | 1/2003 | Prausnitz et al. | |
| 6,511,463 B1 | 1/2003 | Wood et al. | |
| 6,558,361 B1 | 5/2003 | Yeshurun et al. | |
| 6,603,987 B2 | 8/2003 | Whitson et al. | |
| 6,770,480 B1 | 8/2004 | Cahham | |
| 6,815,360 B1 * | 11/2004 | Canham et al. | 438/706 |
| 6,855,372 B2 | 2/2005 | Trautman et al. | |

(Continued)

*Primary Examiner*—Nicholas D Lucchesi
*Assistant Examiner*—Laura A Bouchelle
(74) *Attorney, Agent, or Firm*—Gary M. Nath; Joshua B. Goldberg; Charles D. Niebylski

(57) ABSTRACT

High-aspect-ratio microdevices comprising microneedles, microknives and microblades and their manufacturing methods are disclosed. These devices can be used for the delivery of therapeutic agents across the skin or other tissue barriers to allow chemical and biological molecules getting into the circulation systems. The microneedles can also be used to withdraw body fluids for analysis of clinically relevant species when the device has an integrated body fluid sensor or sensor array in the vicinity of microneedles.

6 Claims, 6 Drawing Sheets

U.S. PATENT DOCUMENTS

| | | | |
|---|---|---|---|
| 2002/0138049 A1* | 9/2002 | Allen et al. | 604/272 |
| 2002/0177839 A1* | 11/2002 | Cormier et al. | 604/500 |
| 2004/0060902 A1 | 4/2004 | Evans et al. | |
| 2004/0181203 A1 | 9/2004 | Cormier et al. | |
| 2004/0241965 A1 | 12/2004 | Merritt et al. | |
| 2005/0065472 A1 | 3/2005 | Cindrich et al. | |
| 2005/0080028 A1 | 4/2005 | Catchpole et al. | |
| 2005/0085766 A1 | 4/2005 | Trautman et al. | |
| 2005/0096586 A1 | 5/2005 | Trautman et al. | |
| 2005/0096632 A1 | 5/2005 | Pettis et al. | |

* cited by examiner

HIGH-ASPECT-RATIO MICRODEVICES AND METHODS FOR TRANSDERMAL DELIVERY AND SAMPLING OF ACTIVE SUBSTANCES

CROSS-REFERENCE TO RELATED APPLICATIONS

The present application claims priority to U.S. provisional application No. 60/521,540, filed on May 18, 2004, the teachings of which are incorporated herein by reference.

FIELD OF THE INVENTION

The present invention relates to high-aspect-ratio microdevices and the method of making and using the same. The microdevices referred here include microneedles, microneedle arrays, microblades, microblade arrays, microknives, and microknife arrays.

BACKGROUND OF THE INVENTION

Drugs are commonly administered in solid form through pills or capsules that can be orally taken. However, many biological drugs can not be administered this way because of degradation in the gastrointestinal tract and quick elimination by the liver. Another common technique for administration of drugs in liquid form is through injection using a metal hypodermic needle that can cause significant pain and discomfort to patients. A number of physical and chemical techniques including electroporation, laser ablation, ultrasound, thermal, iontophoresis and chemical enhancers have been explored to develop painless transdermal drug delivery techniques. It was found that it's very difficult for the molecules with a molecular weight higher than 500 or diameter larger than 1 nm to penetrate normal human skin. Further studies showed that the key barrier for transdermal delivery of substances is the stratum corneum layer, the outer layer of skin, that is about 4-30 micron thick. Invasive methods to overcome this skin barrier have been used in practice, such as intradermal (ID), intramuscular (IM) or subcutaneous (SC) injection using standard hyperdomic needles and syringes. These methods cause pain and require a skilled professional. In addition, they may cause needle injuries. Similarly, current method of extracting biologic fluids such as blood from patients suffers from the same disadvantages.

In order to improve the skin permeability of the therapeutic agents and other active ingredients, microneedles have been recently developed to disrupt the stratum corneum and facilitate the delivery of the active agents and ingredients to the epidermis. These active substances can then diffuse through the rest of epidermis to the dermis and absorbed by blood vessels and lymphatics there. The substance absorbed can get into circulation system. Thus both topical and system-level delivery of drugs is possible. Since there are no nerves and blood vessels in stratum corneum and epidermis, this is a minimally invasive, painless and blood-free method of drug delivery. An additional advantage of this method, when engineered for topical delivery of vaccines, can lead to enhanced inoculation effect because the epidermis is rich in antigen presenting cells and is a desired target for vaccine delivery.

The prior art reports many devices and methods to overcome the skin barriers. For example, U.S. Pat. Nos. 5,855,801 and 5,928,207 assigned to The Regents of the University of California taught a microneedle fabrication method similar to IC compatible neural recording arrays. The disclosed microneedle arrays are typically linear array as they are in the plane of the silicon substrate surface. Microneedles have been also fabricated by heating the glass tube and lengthening the heated part till the diameter of the tip is reduced to the desired range. It's in general very difficult to control the size of the needle shaft and the tip this way although biologists are still using this method to produce microneedles that can inject or withdraw substances from a single cell.

U.S. Pat. No. 6,503,231 by Prausnitz et al discloses a method for making out-of-the-plane porous or hollow microneedles. It either involves porous silicon formed by anodization of silicon or deals with sacrificial molds or selective removal of substrate materials to form fluidic conduits. U.S. Pat. No. 6,511,463 by JDS Uniphase Corp. also taught a method to fabricate the same. U.S. Pat. No. 6,558,361 assigned to Nanopass Ltd. taught a method for the manufacture of hollow microneedle arrays by removing a selective area of substrate material. U.S. Pat. No. 6,603,987 assigned to Bayer Corp. also disclosed a method to make hollow microneedle patch. All these methods are trying to perform certain functions of the current hyperdomic needles and create a miniaturized analog to perform drug delivery or extract body fluids without causing pain and discomfort.

More recently, U.S. 2004/0241965 discloses a method of making high aspect ratio electrode arrays comprised of solid metals. It involves the preparation of porous microchannel glass template, electrodeposition of metals in the microchannels, and final preparation of electrode array following electrodeposition. The body of microelectrode is formed by electrodeposition method similar to those used in forming nanowires.

The prior methods to make microneedles, whether they are in-the-plane or out-of-the-plane from the substrate material, are cumbersome and expensive. The hollow microneedle arrays, while their sizes are scaled down from conventional needles, are especially expensive to make because of complexity in fabrication process. Their mechanical integrity also suffers as their sizes become smaller. Accordingly, a continuing need exists for an improved low cost, disposable transdermal delivery device for effective through skin delivery of substances in a controlled manner.

SUMMARY OF THE INVENTION

The present invention provides methods for making high-aspect-ratio microneedles, microblades and microknives. Whether they are integrated with microchannels and microreservoirs or not, these microdevices can serve as a platform for painless drug delivery or as sensors and sensor arrays for analysis of a patient's body fluids.

Little has been mentioned in the prior art on using solid microneedle to achieve efficient and efficacious transdermal delivery. It's unobvious that solid microneedle, solid microblades and solid microknives can be practically usable to deliver therapeutically meaningful dosage because there are no obvious fluidic conduits for fast transport or injection of fluidics. It is unexpectedly found that the conduit opened up in the stratum corneum by piercing solid microneedles through skin can not be completely closed even after the removal of microneedles. It is therefore the primary object of the present invention to provide a two-step method for efficient and efficacious delivery of drug compounds, vaccines and active cosmetic substances through skin. The first step is the application of a microdevice comprising microneedles, or microblades, or microknives to the skin and open up hundreds or thousands of pathways in the stratum corneum layer. The length of needle or blade or knife is such that penetration depth does not reach dermis layer to cause any pain or discomfort. The second step is to immediately remove the microdvice and apply a skin patch that has active substances embedded in it for controlled release of these substances. In this regard, we disclose a safe, painless, and convenient method for transdermal delivery of substances such as drugs, vaccines and cosmetic compounds.

Another objective of this invention is to disclose methods of microdevices fabrication that can yield microdevices array with improved mechanical strength using a combination of isotropic and anisotropic etch.

It is yet another object of the present invention to fabricate microdevices devices for controlled release of substances for an extended period.

Another object of the present invention is to fabricate high-aspect ratio microneedles with increased needle length and sensors are placed in the vicinity of microneedle base, leading to a minimally-invasive diagnostic system. Sensor arrays are used to improve their selectivity. Compared to microneedles for drug delivery, microneedles with integrated sensors are larger to assure sufficient sampling of body fluids and their mechanical integrity can be assured.

BRIEF DESCRIPTION OF THE DRAWINGS

FIG. 9 shows level of cumulative amount permeated through skin measured in vitro for Botulinum Toxin Type A and Bovine Serum Albumin with microneedle treatment using the method disclosed in the current invention.

FIG. 10 shows interferon-alfa-1b activity measured in vivo on rabbit with $4.8 \times 10^7$ IU interferon-alpha-1b administered using method disclosed in the current invention as compared to subcutaneous injection of the same amount of interferon-alfa-1b.

DETAILED DESCRIPTION OF THE INVENTION

The present invention provides high-aspect-ratio microstructures (HARMS) and methods of manufacturing the same, as well as their applications in delivery of drugs, vaccines, diagnostic agents and cosmetic substances and sampling of body fluids.

Figure 1:
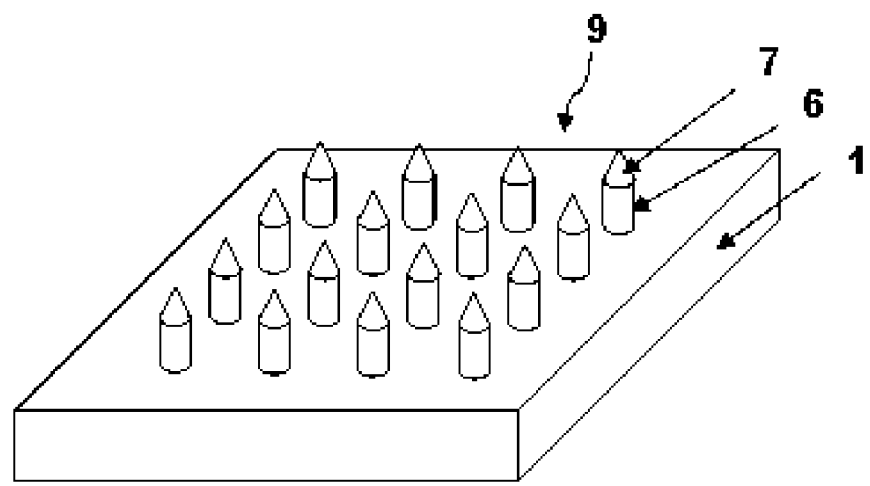
FIG. 1 is a schematic view of an embodiment of a microneedle array formed using the disclosed process flow illustrated in FIGS. 6A-6H.

Referring to FIG. 1, the preferred embodiment is a microdevice 9, having a body 7 and a sharp tip 6 in the case of microneedles or sharp edge 6 in the case of microblades and microknives. The body 7 and sharp tip 6, being out-of-plane on the substrate 1 are covered by a biocompatible coating 8 as illustrated in FIG. 6H. They may have embedded microchannels, connecting to microreservoirs where the active substances are stored.

Aspect-ratio is defined as the ratio of the depth or height of a structure to its lateral dimension. High-aspect-ratio microstructures typically have an aspect ratio higher than about 5:1 and they may be useful for a variety of purposes. In the current invention, the tip of microneedle 6 or the edge of the microblade and microknife 6 needs to be sharp in order to lower the insertion force, while the body of microdevice 7 should be high enough to allow it to completely penetrate stratum corneum. A typical size of the needle tip or width of edge on microbaldes and microknives is smaller than 10 microns, preferably smaller than 5 microns and the height of the microdevices is higher than 20 microns, preferably higher than 50 microns. The aspect ratio of these microdevices, in a preferred embodiment of the current invention, are higher than 10:1 with the size of the tip and edge smaller than 5 microns and the height of microdevices higher than 50 microns. HARMS can thus be used to fabricate microdevices including microneedles, microblades, and microknives for drug delivery through skin or body fluids extraction out of skin. Another example of HARMS is microchannels for microfluidic manipulation and transport. HARMS is typically made by Micro-ElectroMechanical Systems (MEMS) or microfabrication technology that involves a number of thin film deposition, photolithography, etching and electroplating, injection molding, hot embossing, as well as LIGA process.

Skin Structure

Skin has a biological barrier called stratum corneum in its outer layer. This layer of about 20 microns thick prevents most of the molecules from penetrating through the skin. So far, the successful skin patch is only able to deliver drug molecules of less than 500 Da and these small molecules are typically limited to hydrophobic ones.

The layer below the stratum corneum is called viable epidermis. Epidermis is between 50 to 100 micron thick. The viable epidermis layer has no blood vessels and the molecules in this layer can be transported to and from the dermis, a layer under the viable epidermis, which is between 1 to 3 mm thick. There are blood vessels, lymphatics and nerves in dermis layer.

Requirement of Delivery of Drugs, Vaccines and Cosmetic Substances

Successful transdermal delivery of therapeutic drugs, vaccines and cosmetic substances needs a way to transport molecules, especially large molecules through the skin barrier, stratum corneum. The substance can be delivered into the skin in any form acceptable to pharmaceutical requirements, but a gel formulation is preferred to achieve controlled release of active ingredients.

The Microneedles

Figure 2:
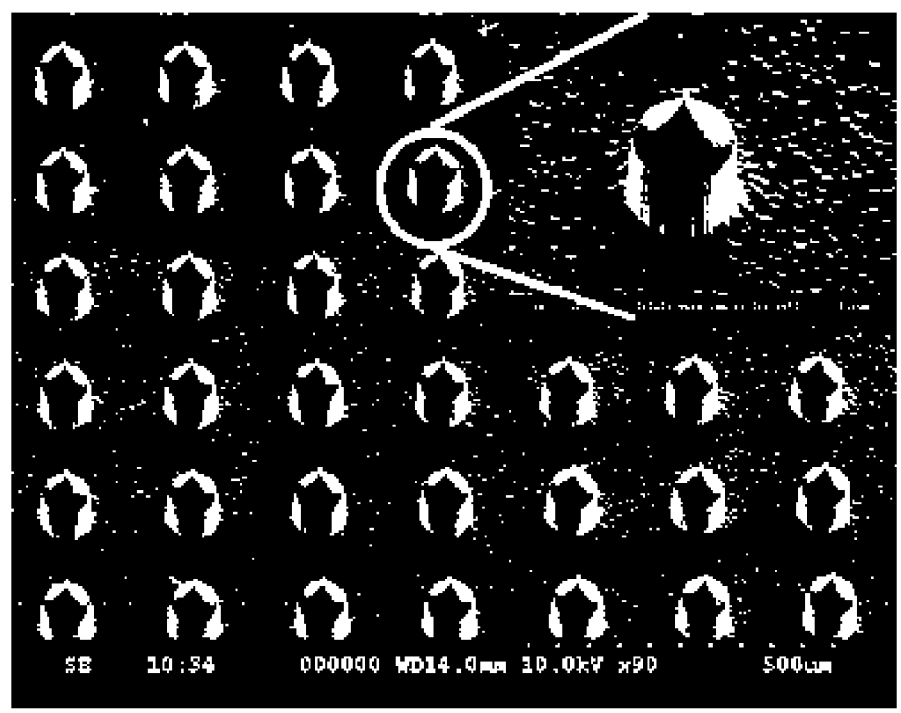
FIG. 2 is a scanning electron microscope micrograph of a microneedle array fabricated using the method disclosed in the Example 1 and illustrated in FIGS. 6A-6H.
Figure 3:
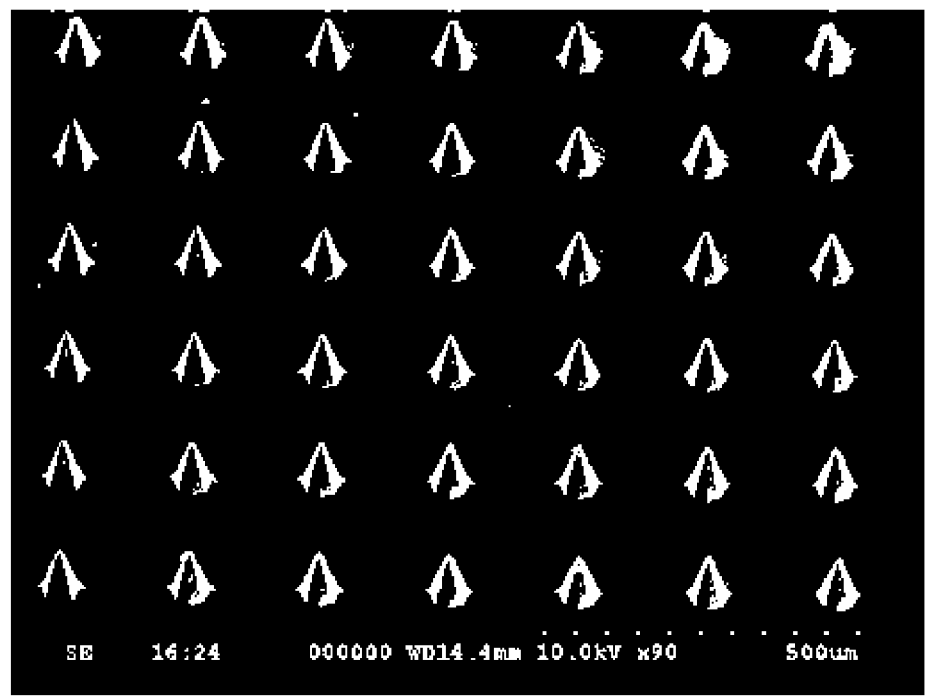
FIG. 3 is a scanning electron microscope micrograph of microneedle array fabricated using the method disclosed in the Example 2

The microneedle devices disclosed herein can contain one or more microneedles. The length of the microneedle is typically in the range of 20-500 microns, sufficient to pierce through the outer skin barrier layer and deliver molecules to viable epidermis or even deeper. The diameter of a single microneedle is typically in the range of 30-300 microns with a sharp tip of less than 10 microns to cause little comfort to the patients while maintaining mechanical integrity. In one emobodiment of the invention, the needle tip 6 is less than 2 microns and the height of the needle shaft 7 is about 100 microns. The aspect ratio is 50:1. Referring to FIG. 6H, the angle of the tip 10 is between 30 to 75 degree, typically between 45-72 degree. FIG. 2 shows a micrograph of microneedle arrays fabricated by this method with a zoom in view of a single microneedle that has a base diameter of about 80 microns. In another embodiment, FIG. 3 provides a micrograph of a "pyramid-like" microneedles with a base size of about 80 microns. The size of the microneedles is bigger for collection of body fluids and they need to reach the dermis layer in the skin. In one emobodiment of the current invention, the inner diameter of needle tip is about 10 microns and the height of needle is about 1200 microns to allow sufficient extraction of body fluids. The aspect ratio is 120:1.

The Microblades and Microknives

Figure 4A:
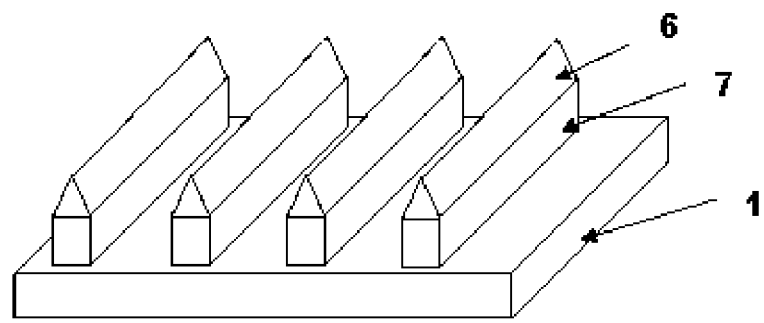
FIGS. 4A and 4B are perspective illustration and side cross-sectional view of microknives.
Figure 4B:
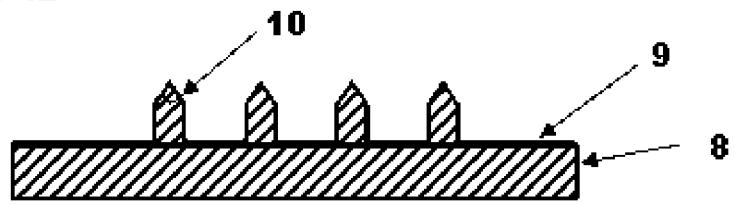
Figure 5A:
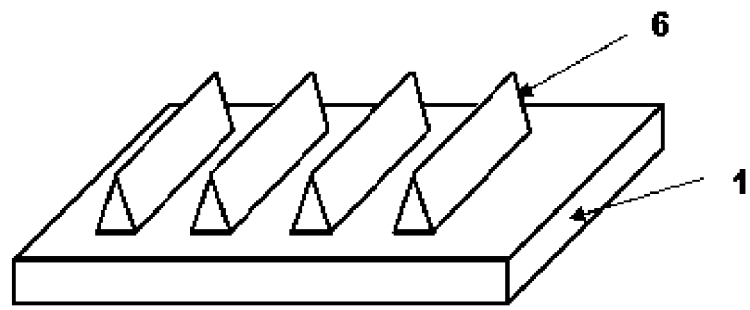
FIGS. 5A and 5B are perspective illustration and side cross-sectional view of microblades.
Figure 5B:
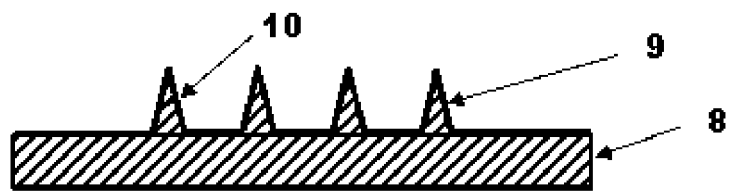

As shown in FIGS. 4 and 5, the microblades and microknives disclosed herein can contain one or more blades or knives. The sharp edge 6 of these devices is below 10 microns wide and the height of the body is more than 100 microns. In a preferred embodiment of the current invention, the edge 6 is below 3 microns and the body height 7 is about 150 microns. The skin contact area is about 0.003 mm×1 mm for each microblade or microknife. The leading angle 10 of the blade edge is between 30 to 75 degree, preferably between 45-72 degree. It will become apparent from the following detailed description of the examples that the difference in manufacturing of microblade and microknife with respect to microneedle is only the shape of the mask using a cross-sectional illustration of the fabrication process disclosed in FIG. 6A-6H.

Materials and Device Sterilization

The devices can be made of many different materials or their combinations, including metals, ceramics, polymers and glass. Examples of the materials are titanium, stainless steel, nickel, alloy of nickel-iron, silicon, silicon oxide, glass, polymethyl methacrylate (PMMA), polyaryletherketone, nylon, PET, poly(lactic acid), poly(glycolic acid) (PGA), poly(lactic-co-glycolic acid) (PLGA), polycarbonate, and polystyrene. It should have enough mechanical strength to penetrate skin without break and buckle while ensure delivery of drugs, or collect of biological fluids. They can be sterilizable using established protocols (see, for example, moist heat, ethylene oxide or radiation sterilization as stated by ANSI/AAMI/ISO 11134:1993, ANSI/AAMI/ISO 11135:1994 and ANSI/AAMI/ISO 11137:1994).

The Microchannels

High-aspect-ratio microchannels can be embedded in microdevices to allow flexible manipulation of microfluidics and connect microneedles to other functional blocks such as drug reservoirs. Microchannels can be made of many different materials or their combinations, including metals, ceramics, polymers and glass.

The Microreservoirs

The microdevices can be connected to a reservoir with drug molecules and their proper formulations in liquid or solid forms. Microreservoir can be made of many different materials or their combinations, including metals, ceramics, polymers and glass. In a preferred embodiment, the microneedles are solid and the microreservoir is connected to the skin surface through microchannels. The gel containing active component can be dissolved by moisture evaporated from skin and the active substance can diffusion into skin through conduits opened along the interface of skin and microneedles. In another embodiment, the microneedles are hollow and they can be connected with drug reservoir through various microchannels. The reservoir can be made of natural polymers, deformable elastic polymers, metals and ceramics as listed above.

Method of Use

The device described herein can be used to treat, prevent, or ameliorate a body condition in need to treatment. The body condition can be a medical condition or a cosmetic condition. Representative medical conditions include, but are not limited to, AIDS, breast cancer, melanoma, liver cancer, lung cancer, blood cancer, pituitary tumors, other cancers, flu, infection, blood disease, cardiac disease, back pain, neck pain, body pain, general pain, arthritis, osteoporosis, headache, depression, smoke, alcoholic, overweight and obesity, menopause, facial hair growth, balding, polycystic ovary syndrome, need of inoculation, need of anesthetics and in particular dermal disease. Representative cosmetic conditions include, but are not limited to, skin aging, skin wrinkle, dark spot, skin discoloration, moisturizing, skin lightening, skin whitening, skin firming, skin lifting, acne, wart, infection, irritation, dry skin and oily skin.

The microdevices of this invention are designed as disposable or re-usable devices. In one embodiment, the microdevices are disposable. Depending on whether the microdevices have coating of active substances on them or not, there are three categories of applications in the delivery of drugs, cosmetic substances and vaccines in the preferred embodiment.

For delivery of a drug, vaccine or cosmetic substance, in one embodiment, the microdevices can be used to perforate or scratch stratum corneum. They are then removed immediately and a skin patch with active substance is applied to the microdevice treated area right away. The skin patch will stay on the skin for a pre-defined period, providing sustainable controlled release of active substances.

Another embodiment is to store the active agents, as defined below, in the substrate and rely on passive diffusion when the microdevice is in touch with skin.

In yet a further embodiment, one can pre-coat microneedle shaft with a formulation that contains active substances. The coated microneedles are applied to the skin and stay on the skin for the entire period of treatment. The rate of through skin transport can be measured using in vitro or in vivo methods known in the art.

Figure 7:
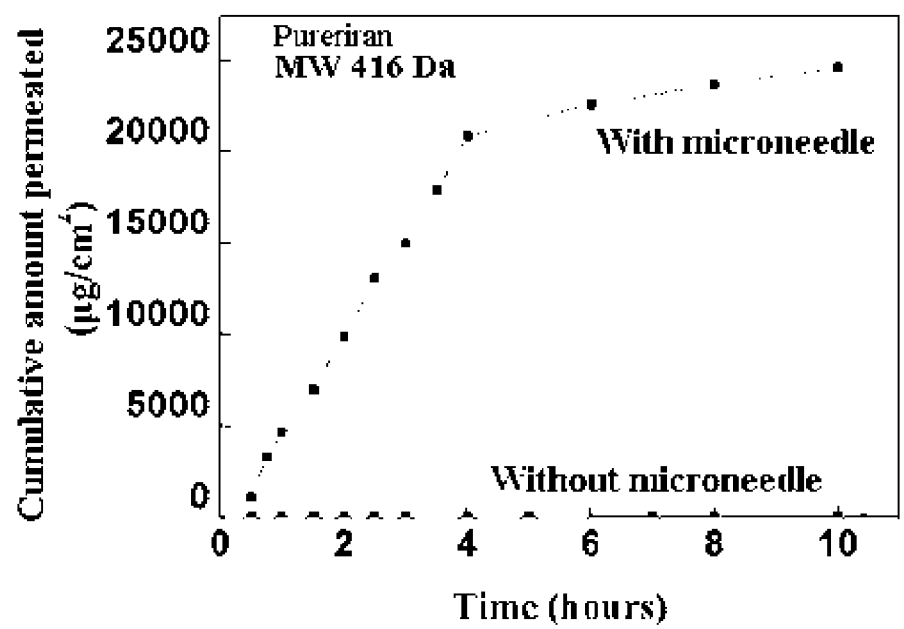
FIG. 7 shows level of cumulative amount permeated through skin for pureriran with and without microneedle treatment in an in vitro test using the method disclosed in the current invention.
Figure 8:
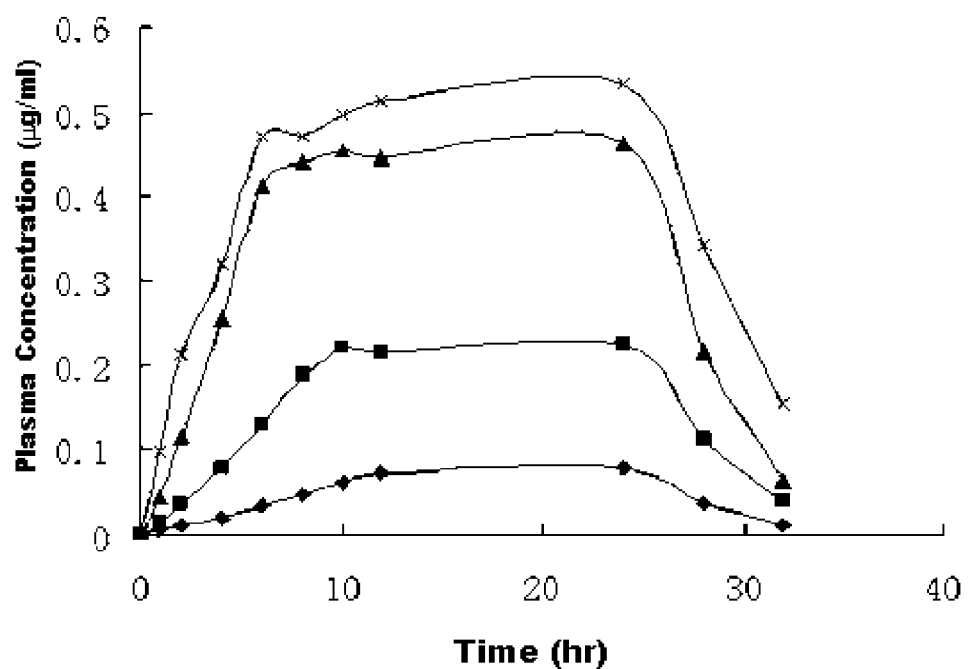
FIG. 8 shows plasma concentration of fluorescence-labeled bovine serum albumin in rabbit tested in vivo at BSA loading in carbopol 934P of 0.15%, 0.20%, 0.25%, 0.30% (Weight/Volume) for each microneedle array that has 400 microneedles. The total formulation amount is 1 mg on microneedle arrays.
Figures 9, 10:
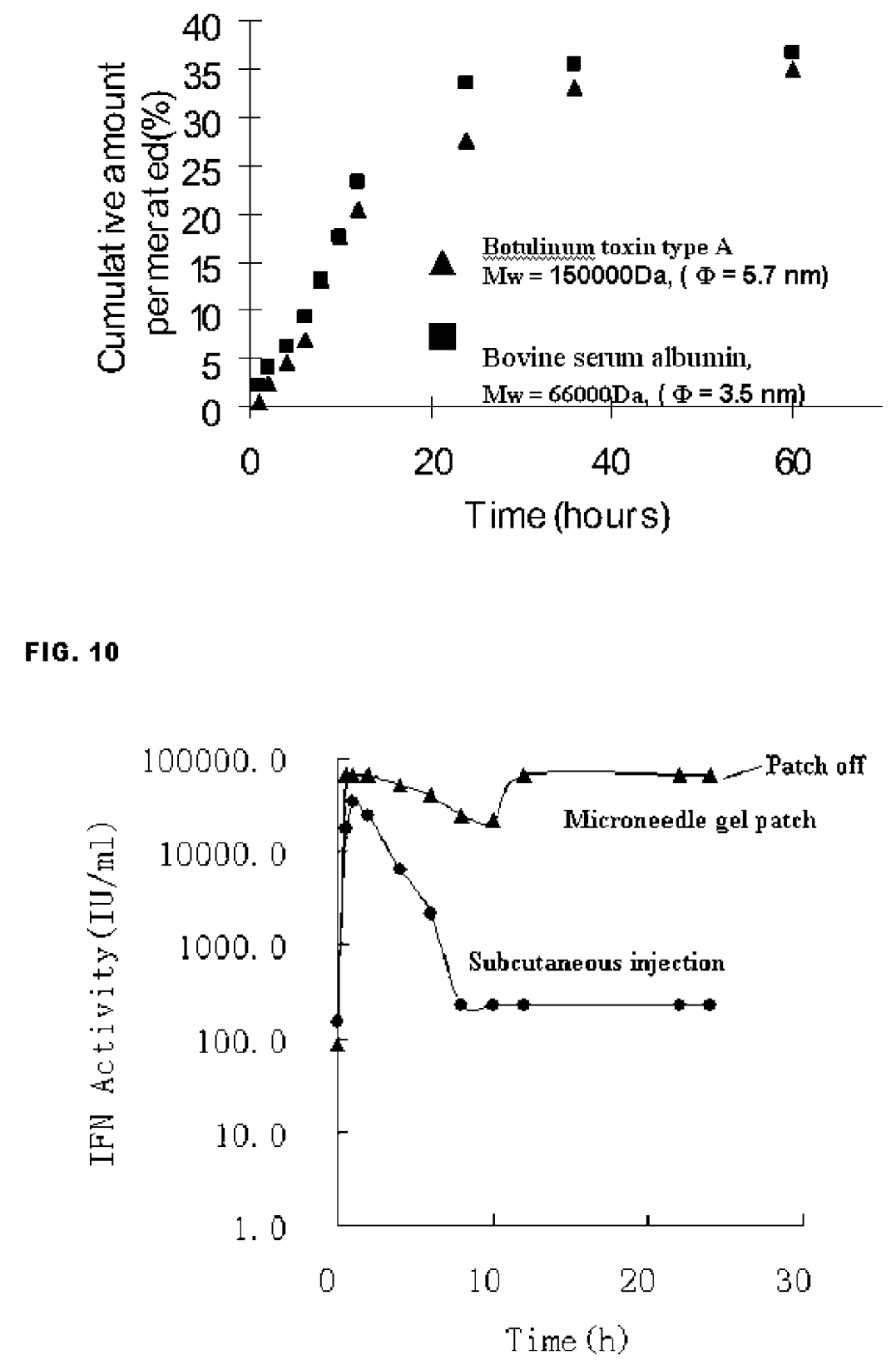

Referring to FIGS. 7-10, the microdevices disclosed herein are effective in increasing the through skin diffusion of molecules, especially therapeutic molecules with molecular weight higher than 500 Daltons and hydrophilic molecules to transport through skin barrier. As it will be further explained in the Examples, the enhancement of transdermal transport was also observed for small molecules with molecular weight lower than 500 Daltons as shown in FIG. 7, as well as large molecules with molecular weight higher than 500. Because of the height of microneedles and microblades is limited, it will not reach the nerve-rich dermis layer and cause any discomfort to the subject.

Active Agent

Active agent or active substance that can be delivered using microdevices are therapeutic agents. The term "therapeutic agent" is used here to refer to active agent that can treat, prevent, ameliorate a body condition or skin condition that needs treatment. A list of examples includes: drugs, vaccines, peptides, proteins, genes, DNAs, nutraceuticals and cosmetics. The drugs can be administered topically and at whole system level. Examples of the drugs as active agents include, but not limited to antibiotics, hormones, steroids, anti-inflammatory drugs, protein drugs, DNA drugs whether natural or synthesized, such as Recombinant Erythropoietin (rhEPO), Taxol®, Interferon-alpha-1b, Interferon beta, Interferon gamma, Emla®, Fluorouracil, Lidocaine, Salicylic acid, Pureriran, eflornithine hydrochloride, spironolactone, flutamide, insulin, nanoparticle drugs, Epidural, recombinant human parathyroid hormone, growth hormone, thyroid, cortisol, estrogen, progesterone, and testosterone. Examples of vaccines active agents include, but not limited to: vaccine against influenza (flu), diphtheria, tetanus, pertussis (DTaP), measles, mumps, rubella (MMR), hepatitis B, polio, haemophilus influenzae type b, chickenpox, tuberculosis, anthrax, yellow fever, rabies, AIDS, cancers, meningococcus, SARS and cholera. More examples of cosmetic substances as active agents include, but not limited to: botulinum toxin type A, hyaluronic acid and its derivatives, acetyl hexapeptide-3, vitamin A, vitamin C, vitamin E, alpha-hydroxyacids, collagen and hormones. Diagnostic reagents are also included. Examples include, but not limited to: quantum dots, functionalized nanoparticles, magnetic particles for diagnostic purpose.

Drug Delivery

In one aspect, the present invention provides a device 10 for delivery of therapeutic active agent as defined above across the skin barrier, stratum corneum layer. Once the substances pass the stratum corneum, there is less resistance for the substances to diffuse into the subsequent layers of the skin: epidermis and dermis. The substances will be absorbed by microvessels and lymphatics in the dermis layer and delivered to entire human body. Microdevices disclosed in the current invention can enhance through skin penetration of molecules of molecular weight lower than 500 Dalton as shown in FIG. 7. Microdevices can also enable through skin transport of large molecules of molecular weight higher than 500 Dalton as shown in FIGS. 8, 9 and 10. The molecular weight of Bovine Serum Albumin is 66,000 Dalton. The molecular weight of Botulinum Toxin Type A is 150,000 Dalton and the molecular weight of Interferon-Alpha-1b is 17,000 Dalton.

Topical Delivery of Cosmetic Substances

It's known to one in the art that certain substances have specific functions as cosmetics. For example, Botulinum Toxin Type A is a toxin that blocks neuromuscular transmission when it is injected in small amounts (e.g., 10 units per 0.1 ml injection volume) into specific muscles to treat and reduce wrinkles on the face. The maximum dosage recommended as a single injection for any one muscle at any spot is 25 units. If overdosed or the injection is incorrectly performed, the patient can be left with an immobile face or droopy eyelids till the effect of the injection wears off. The side effects include numbness, swelling and headaches. Administered through microdevices disclosed in the current invention, it's possible to provide a controlled release of Botulinum Toxin Type A and keep an optimal local concentration to achieve the best result while minimize the side effects. In a preferred embodiment of this invention, gel patch with botulinum toxin type A is applied to the skin pre-treated with microneedle array. A significant increase in through skin penetration of botulinum toxin type A was observed as detailed in FIG. 9. No through skin transport was observed without application of microdevices. More examples were provided in the above "active agents" section.

It's also evident that through skin transport on microdevices treated skin has less dependency on molecular weight as observed in FIG. 9. Using the methods described herein, practically, any cosmetic substances can be delivered using microdevices herein. Local concentration can be adjusted through loading and formulation for controlled release. In one embodiment of this invention, one can deliver hyaluronic acid gel through diffusion enhanced by microdevices. Hyaluronic acid is a substance that exists naturally in the body. A major important function of hyaluronic acid is to carry and bind water molecules. Stabilized non-animal hyaluronic acid does not contain animal protein and does not require a skin test prior to treatment. It's thus a preferred embodiment of this invention to use microdevices to delivery locally stabilized non-animal hyaluronic acid to treat wrinkles and facial lines.

Yet, in a further embodiment of this invention, one can locally delivery collagen by microneedles, e.g., for allergic skin test and controlled release of collagen into the skin.

Yet, another embodiment of this invention is to provide for local delivery of acetyl hexapeptide-3. This molecule is a non-toxic, non-irritant compound that modulates the excessive stimulation of the facial muscles, relaxing facial tension and it can reduce and prevent the formation of new wrinkles due to over-stimulation of facial muscles. More examples include but not limited to: vitamin A, vitamin C, vitamin E, alpha-hydroxyacids, and hormones.

Delivery of Vaccines

In a further aspect of the present invention, the method provided herein can be used for topical delivery of vaccines below the stratum corneum layer. The type of vaccines includes conventional vaccines as well as protein, peptide, DNA vaccines and the like as previously described.

Controlled Release

The microdevices need to deliver drug molecules through skin at a rate that is sufficient to maintain a therapeutic useful concentration in plasma. The size, density of the microdevices can be adjusted to meet the delivery requirement. The microdevices can be further coated with a formulation that contains active therapeutic molecules, or vaccines, or cosmetic substances, together with polymer binders such as chitosan, carbopol 934P, cellulose and starch to form a dry film. Additional additives of rheology modifiers, surface active agents, stabilizer, rehydration agents may be used. The special formulation can control the dissolve rate of the active drug molecule and regulate the drug release rate. One example for controlled release of bovine serum albumin is shown in FIG. 8. The microdevices may be integrated with embedded microfluidic channels that connect to microreservoirs.

The Integrated Sensors

It is another aspect of the invention to provide a device in which clinical biosensor and/or sensor arrays are fabricated in the close vicinity of these HARMS structures. For example, microneedle can collect an extremely low sample volume of body fluids from a patient and allow rapid point-of-care analysis of body fluids. In one embodiment, the sample volume extracted is below 0.1 microliter, typically around 0.01 microliter.

Methods for HARMS Fabrication

The HARMS were fabricated using MEMS microfabrication technology. The typical fabrication process involved lithography, wet etch and dry etch, thin film deposition and growth, electroplating, as well as injection molding and hot embossing. One example of fabrication method was to use Bosch process that allowed deep Si etch (www.oxfordplasma.de/process/sibo_1.htm). It formed HARMS suitable either as device body or mold for further processing. The aspect ratio was higher than 5:1, independent to feature size and pattern shape as long as the features can be defined by lithography. Another fabrication method was KOH or TMAH wet etch of single crystal Si substrate that is <100> orientation or <110> orientation. Yet another fabrication method was using HF solution to electrochemically form porous Si structures (www.techfak.unikiel.de/matwis/amat/poren/ps.html). Metals was used for the fabrication of HARMS through a maskless process called electropolishing starting from a structure fabricated by traditional machining methods such as cutting, electro-discharge machining, milling, grinding, polishing and drilling (www.najet.com and www.fischion.com/product_support/model_110_application_notes.asp). Use of any single method herein or a combination of these methods as further disclosed in the examples below led to the form of desired HARMS disclosed in the current invention.

EXAMPLE 1

Fabrication of Si Microneedles

Bosch etch process is a widely used MEMS process that is known in the art to etch deep vias and trenches. The current invention disclosed a method that involved isotropic etch first to form microneedle tip 6 and second anisotropic Bosch etch later to form microneedle shaft 7 as shown in FIG. 6G.

Figure 6A:
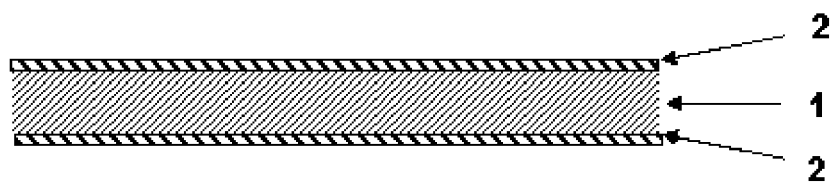
FIG. 6A to 6H are cross-sectional illustration of a fabrication process flow of a preferred method to form microdevices.
Figure 6B:
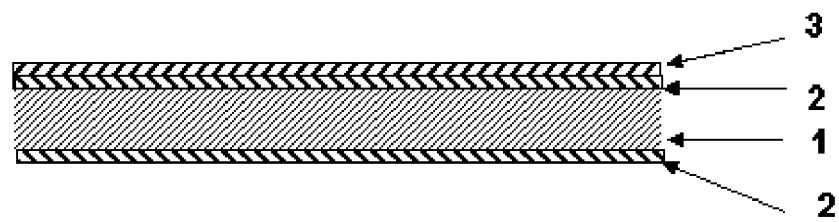
Figure 6C:
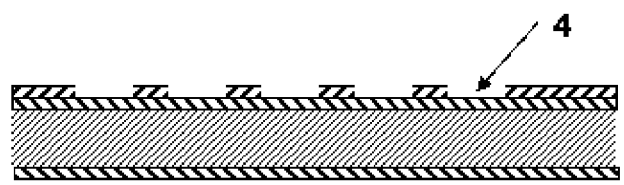
Figure 6D:
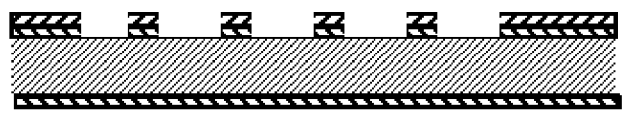
Figure 6E:
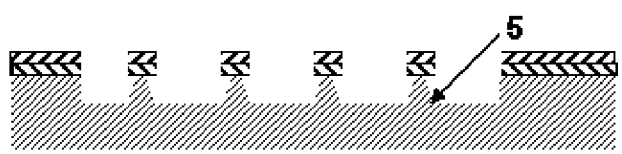
Figure 6F:
Figure 6G:
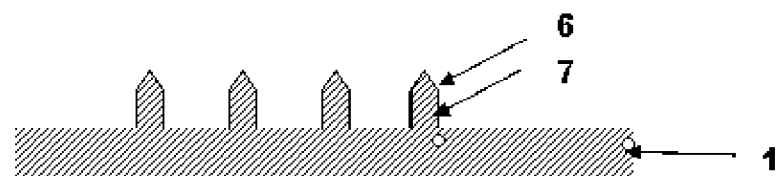
Figure 6H:
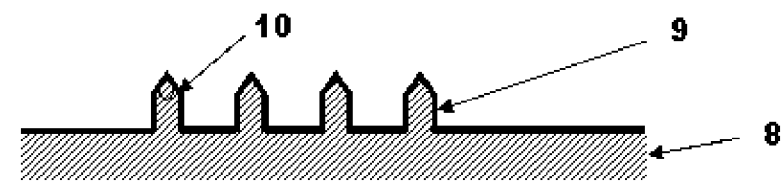

Referring to FIG. 6A, a silicon wafer 1 of any crystal orientation with about 1 micron of thermal oxide 2 coated on both sides was used as substrate. Doping level in the silicon substrate was found to be not critical. A chromium layer with thickness ranging between 0.2 to 20 nm was sputtered onto the substrate. A layer of photoreist 3 was applied to front side of the wafer as shown in FIG. 6B. It was patterned into a number of circular islands with a diameter that was equal to the base of the microneedles as shown in FIG. 6C. The shape of the pattern was changed to rectangular to form microknives and microblades. The Cr etch was done using common method that have been known in the art. Cr film serveed as hard mask to etch part of oxide and silicon substrate 4. Oxide 2 was patterned, as shown in FIG. 6D by either buffered oxide etch in solution or dry etch using $CHF_3$ or $CF_4$ as etching gases. In a preferred embodiment of the current invention, an isotropic etch of Si was done using $SF_6$ only while the Cr and oxide mask materials were still there as shown in FIG. 6E. The undercut of Si substrate 1 formed the tip 5 of the microneedles as shown in FIG. 6E. Once Si undercut reacheed the stage with about 20 microns left, Bosch process was used to perform alternative deposition and etch cycles until the etch depth reached the pre-defined length of microneedles as shown in FIG. 6F. The final shape of microneedles was formed by a short wet etch using a mixture of acetic acid, nitric acid and fluoric acid, known as HNA to the people in the art. HNA dip helped release the hard mask and sharpen the tip 6 of the microneedle as shown in FIG. 6G. The formed microneedle was coated with about 200-500 A Ti coating to improve biocompatibility as shown in FIG. 6H. FIG. 2 shows a micrograph of microneedles fabricated in this way.

EXAMPLE 2

Fabrication of Si Microneedles

The current invention also disclosed a method that did anisotropic etch first to form microneedle body and switch to orientation dependent etch (ODE) later to form microneedle shaft and tip.

A silicon wafer of <100> orientation with 0.5-3 micron of thermal oxide coated on both side was used as substrate as shown in FIG. 6A. The oxide was patterned into a number of circular or square islands with a diameter that was roughly equal to the base of the microneedles. In one example, the diameter of the circular pattern was about 100 micron. The oxide etch was done by either buffered oxide etch in solution or dry etch using $CHF_3$ or $CF_4$ as etching gases. Once silicon oxide etch was completed, Bosch process was used to perform alternative deposition and etch cycles until the etch depth reaches the pre-defined length of microneedles, yielding a number of circular or square posts on the silicon substrate. The final shape of microneedles, as shown in FIG. 6G was formed by KOH etch in a heated bath at a temperature between 20-90 degree. The KOH concentration was between 10% to 80%. Typically, the etch temperature was between 50 to 80 degree and potassium hydroxide (KOH) concentration was between 20-50%. Tetramethyl ammonium hydroxide (TMAH) or sodium hydroxide was used to replace KOH to give similar results. Typical etch condition was 20%-40% TMAH at about 80 degree. About 500 A Ti coating was applied to the formed microneedles to improve biocompatibility as shown in FIG. 6H. FIG. 3 shows microneedle array fabricated in this way.

EXAMPLE 3

Fabrication of Microblades and Microknives

As shown in FIG. 6C, if the pattern is a rectangular shape, the microdevices formed according to the process flow disclosed in the Examples 1 and 2 become microknives and microblades.

EXAMPLE 4

Fabrication of Polymer Microneedles

A stainless steel piece was used as cathode. A patterned conductive piece with round posts on it was used as anode. The height of the posts was comparable to microneedle height. Both electrodes were immersed in an electrolyte and a voltage of 0.5-5 V was applied to them, a selective area of cathode was dissolved away, leaving behind arrays of cavity. Once the etch was complete, the stainless steel piece with microneedle body in the shape of cavity was obtained. It was used as mold insert for micro-injection molding to obtain polymeric microneedles, using materials listed previously.

EXAMPLE 5

Fabrication of Metal Microneedles

A metal piece such as stainless steel, or Ti or Ni was used as cathode. A conductive piece with a grid pattern on it was used as anode. The size of each square was comparable to base of microneedle. When both electrodes were immersed in an electrolyte and a voltage of 0.5-5 V was applied to them, a selective area of cathode were dissolved away, leaving behind arrays of microneddles. The tips 6 of the microneedles were sharpened by electropolishing, yielding very sharp metal microneedle arrays.

EXAMPLE 6

Application of Microdevices

In one embodiment, Chitosan was purified before use as following: A 20 g of chitosan was dissolved in 1 L of 1% acetic acid solution. After it was filtered under reduced pressure, 1 M NaOH was added into the filtrate to produce precipitate. The precipitate was washed repeatedly with de-ionized water until the pH value of rinse water was about 7. The precipitate was dried in a vacuum dry box under reduced pressure. The purified chitosan was milled to powder and was used in preparing stock solution that may further contain additives of rheology modifiers, surface active agents, stabilizer, rehydration agents and a combination of thereof to form a formulation. The known volume of chitosan stock solution containing known amount of active agent was prepared by dissolving active agent in a chitosan stock solution. Skin patch containing active agent was prepared using the casting method in cleanroom environment. The skin patch prepared this way was let dry at room temperature.

The application of microdevice enabled skin patch was a simple two-step procedure. The first step was the perforation or scratch of skin using a microneedles or microknives and microblades with a plastic handler attached to them on the backside with no high aspect ratio microstructures. These microdevices were coated with a biocompatible film and had no active agent on them. This step can also be replaced using a spring-powered mechanical device with microneedle or microknives or microblades loaded. For example, a lancing device with a disposable microneedle attached to the moving end. The second step was the application of skin patch prepared using a method disclosed herein to the microdevice treated skin area. Spring-powered devices provided results with better consistency.

In another embodiment, the microdevice arrays were coated with chitosan formulation and let dry in a dust-free atmosphere at room temperature. The microdevice containing active agent was applied to the skin manually or using a spring powered device. Adhesive tape was used to keep the microdevice on the skin during the entire treatment cycle.

What is claimed is:

1. A method of making a microfabricated device for delivery of an active agent comprising:
   performing a first isotropic etch to define microneedle tips, microblade edge, or microknife edge of the device,
   performing a second anisotropic Bosch etch to define microneedle shaft, microblade body, or microknife body of the device, thereby forming the device, and
   forming the device,
   wherein the microfabricated device comprises a structure formed of a material selected from the group consisting of metals, ceramics, silicon, glass, polymers, and combinations thereof,
   wherein the structure is selected from the group consisting of solid microneedles, solid microblades, solid microknives, and a combination thereof,
   wherein the microneedles, microblades, or microknives have and aspect ration of about 10:1 or higher.

2. A method of making a microfabricated device for delivery of an active agent comprising:
   performing an anisotropic etch first to define the body of microneedle, microblade or microknife device,
   and performing orientation dependent etch of Si using potassium hydroxide or tetramethyl ammonium hydroxide or sodium hydroxide solution, thereby forming the device,
   wherein the microfabricated device comprises a structure formed of a material selected from the group consisting of metals, ceramics, silicon, glass, polymers, and combinations thereof,
   wherein the structure is selected from the group consisting of solid microneedles, solid microblades, solid microknives, and a combination thereof,
   wherein the microneedles, microblades, or microknives have and aspect ration of about 10:1 or higher.

3. A method of making a microfabricated device for delivery of an active agent comprising
   moving one or two electrodes comprising a working electrode which is a cathode and a counter electrode which is an anode during an electrochemical etch to define the body of the microneedle, microblade, or microknife of the device, and
   forming the device,
   wherein the microfabricated device comprises a structure formed of a material selected from the group consisting of metals, ceramics, silicon, glass, polymers, and combinations thereof,
   wherein the structure is selected from the group consisting of solid microneedles, solid microblades, solid microknives, and a combination thereof,
   wherein the microneedles, microblades, or microknives have and aspect ration of about 10:1 or higher.

4. A microfabricated device for delivery of an active agent produced by a process comprising:
   performing a first isotropic etch to define microneedle tips, microblade edge, or microknife edge,
   performing a second anisotropic Bosch etch to define microneedle shaft, microblade body, or microknife body, thereby forming the device, and
   forming the microfabricated device,
   wherein the microfabricated device comprises a structure formed of a material selected from the group consisting of metals, ceramics, silicon, glass, polymers, and combinations thereof,
   wherein the structure is selected from the group consisting of solid microneedles, solid microblades, solid microknives, and a combination thereof,
   wherein the microneedles, microblades, or microknives have and aspect ration of about 10:1 or higher.

5. A microfabricated device for delivery of an active agent produced by a process comprising:
   performing an anisotropic etch first to define the body of a microneedle, microblade, or microknife, and performing orientation dependent etch of Si using potassium hydroxide or tetramethyl ammonium hydroxide or sodium hydroxide solution, thereby forming the microfabricated device,
   wherein the microfabricated device comprises a structure formed of a material selected from the group consisting of metals, ceramics, silicon, glass, polymers, and combinations thereof,
   wherein the structure is selected from the group consisting of solid microneedles, solid microblades, solid microknives, and a combination thereof,
   wherein the microneedles, microblades, or microknives have and aspect ration of about 10:1 or higher.

6. A microfabricated device for delivery of an active agent produced by a process comprising:
   moving one or two electrodes comprising a working electrode which is a cathode and a counter electrode which is a patterned anode during electrochemical etch, and forming the microfabricated device,
   wherein the microfabricated device comprises a structure formed of a material selected from the group consisting of metals, ceramics, silicon, glass, polymers, and combinations thereof,
   wherein the structure is selected from the group consisting of solid microneedles, solid microblades, solid microknives, and a combination thereof,
   wherein the microneedles, microblades, or microknives have and aspect ration of about 10:1 or higher.

* * * * *

UNITED STATES PATENT AND TRADEMARK OFFICE
CERTIFICATE OF CORRECTION

PATENT NO. : 7,591,806 B2
APPLICATION NO. : 10/908584
DATED : September 22, 2009
INVENTOR(S) : Bai Xu Page 1 of 1

It is certified that error appears in the above-identified patent and that said Letters Patent is hereby corrected as shown below:

Column 11, Claim 1, Line 42
Please delete "and aspect ration"
and replace with --an aspect ratio--

Column 11, Claim 2, Line 59
Please delete "and aspect ration"
and replace with --an aspect ratio--

Column 12, Claim 3, Line 13
Please delete "and aspect ration"
and replace with --an aspect ratio--

Column 12, Claim 4, Line 30
Please delete "and aspect ration"
and replace with --an aspect ratio--

Column 12, Claim 5, Line 47
Please delete "and aspect ration"
and replace with --an aspect ratio--

Column 12, Claim 6, Line 62
Please delete "and aspect ration"
and replace with --an aspect ratio--

Signed and Sealed this
Thirteenth Day of December, 2011

David J. Kappos
*Director of the United States Patent and Trademark Office*